United States Patent
Paillard et al.

(10) Patent No.: US 10,123,976 B2
(45) Date of Patent: Nov. 13, 2018

(54) DISPERSION OF POLOXAMER-PROTEIN PARTICLES, METHODS OF MANUFACTURING AND USES THEREOF

(75) Inventors: Alexandra Paillard, Paris (FR); Marie-Claire Venier, Juigne sur Loire (FR); Jean-Pierre Benoit, Angers (FR)

(73) Assignees: INSTITUT NATIONAL DE LA SANTE ETDE LA RECHERCHE MEDICALE (INSERM), Paris (FR); UNIVERSITE D'ANGERS, Angers (FR)

( * ) Notice: Subject to any disclaimer, the term of this patent is extended or adjusted under 35 U.S.C. 154(b) by 1376 days.

(21) Appl. No.: 12/681,225

(22) PCT Filed: Oct. 1, 2008

(86) PCT No.: PCT/EP2008/063147
§ 371 (c)(1),
(2), (4) Date: Aug. 23, 2010

(87) PCT Pub. No.: WO2009/043874
PCT Pub. Date: Apr. 9, 2009

(65) Prior Publication Data
US 2010/0310669 A1    Dec. 9, 2010

(30) Foreign Application Priority Data
Oct. 1, 2007  (EP) .................... 07291188

(51) Int. Cl.
| | | |
|---|---|---|
| *A61K 9/50* | (2006.01) |
| *C07K 1/02* | (2006.01) |
| *C12N 11/00* | (2006.01) |
| *A61K 38/47* | (2006.01) |
| *A61K 38/18* | (2006.01) |
| *A61P 31/04* | (2006.01) |
| *A61K 9/51* | (2006.01) |
| *A61K 9/16* | (2006.01) |

(52) U.S. Cl.
CPC .......... *A61K 9/5146* (2013.01); *A61K 9/1641* (2013.01); *A61K 9/1694* (2013.01); *A61K 9/5031* (2013.01); *A61K 9/5089* (2013.01); *A61K 9/5192* (2013.01)

(58) Field of Classification Search
None
See application file for complete search history.

(56) References Cited

U.S. PATENT DOCUMENTS

| | | | | |
|---|---|---|---|---|
| 5,118,528 | A * | 6/1992 | Fessi et al. ............... 427/213.36 |
| 2001/0006678 | A1* | 7/2001 | Takada et al. ................. 424/460 |
| 2002/0048610 | A1* | 4/2002 | Cima et al. ................... 424/725 |
| 2003/0077329 | A1* | 4/2003 | Kipp et al. ..................... 424/489 |
| 2005/0181041 | A1* | 8/2005 | Goldman ....................... 424/456 |
| 2005/0276861 | A1* | 12/2005 | Kipp et al. ..................... 424/489 |
| 2007/0080323 | A1* | 4/2007 | Joabsson et al. ........ 252/299.01 |
| 2007/0092575 | A1 | 4/2007 | Balaban et al. |

FOREIGN PATENT DOCUMENTS

| | | |
|---|---|---|
| EP | 1598074 A1 | 11/2005 |
| EP | 1658842 A1 | 5/2006 |
| WO | 95/35097 A1 | 12/1995 |
| WO | 97/35563 A2 | 10/1997 |
| WO | 2006/122127 A1 | 11/2006 |

OTHER PUBLICATIONS

Aubert-Pouessel et al., "Preparation of PLGA Microparticles by an Emulsion-Extraction Process Using Glycofurol as Polymer Solvent", 2004, Pharmaceutical Research, 21(12): 2384-2391.*

* cited by examiner

*Primary Examiner* — Robert A Wax
*Assistant Examiner* — Randeep Singh
(74) *Attorney, Agent, or Firm* — Thompson Coburn LLP

(57) ABSTRACT

The present invention relates to a method for preparing poloxamer-protein particles. It also relates to poloxamer-protein particles obtainable by this method, dispersion thereof, and their use in methods of encapsulation, in particular of microencapsulation.

23 Claims, 5 Drawing Sheets

Figure 2:
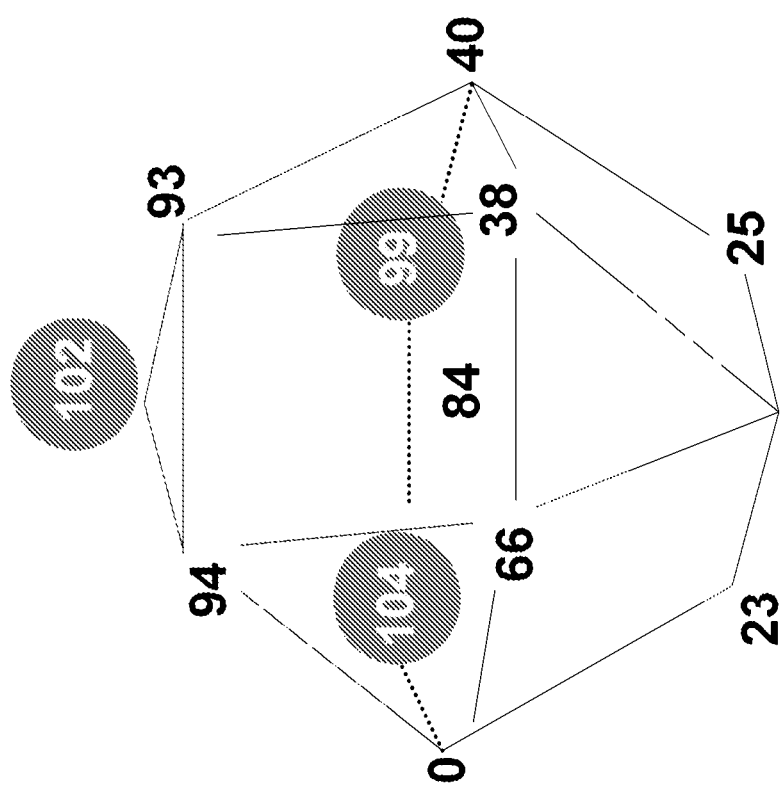

| N°Exp | Ionic strength $U_1$ (M) | Aqueous phase volume $U_2$ (µl) | Protein quantity $U_3$ (mg) |
|---|---|---|---|
| 1 | 0.59 | 90.0 | 0.50 |
| 2 | 0.01 | 90.0 | 0.50 |
| 3 | 0.44 | 155.0 | 0.50 |
| 4 | 0.16 | 25.0 | 0.50 |
| 5 | 0.44 | 25.0 | 0.50 |
| 6 | 0.16 | 155.0 | 0.50 |
| 7 | 0.44 | 111.7 | 0.90 |
| 8 | 0.16 | 68.3 | 0.10 |
| 9 | 0.44 | 68.3 | 0.10 |
| 10 | 0.30 | 133.4 | 0.10 |
| 11 | 0.16 | 111.7 | 0.90 |
| 12 | 0.30 | 46.6 | 0.90 |
| 13 | 0.30 | 90.0 | 0.50 |
| 14 | 0.30 | 90.0 | 0.50 |
| 15 | 0.30 | 90.0 | 0.50 |

*FIG.1*

DISPERSION OF POLOXAMER-PROTEIN PARTICLES, METHODS OF MANUFACTURING AND USES THEREOF

CROSS-REFERENCE TO RELATED APPLICATIONS

This application is a National Stage application of International Patent Application No. PCT/EP2008/063147, filed on Oct. 1, 2008, and incorporated herein by reference in its entirety, which claims the benefit of European Patent Application No. 07291188.6, filed Oct. 1, 2007, and incorporated by reference herein in its entirety.

The present invention relates to a method for preparing poloxamer-protein particles.

It also relates to poloxamer-protein particles obtainable by this method, dispersion thereof, and their use in methods of encapsulation, in particular of microencapsulation.

Protein delivery from microparticles made of biodegradable polymers such as poly(D,L-lactide-co-glycolide) (PLGA) is very interesting to avoid protein proteolysis and complete its sustained release. So, this formulation has been extensively studied. Nevertheless, protein successful delivery from PLGA microparticles is not still achieved. The most important hurdles are related to protein stability issues during the formulation process in one hand and during the release period in the other hand (Schwendeman et al., 1996; van de Weert et al., 2000; Bilati et al., 2005; Tamber et al., 2005; Wang et al., 2005). While protein stabilization during the formulation process is being reached thanks to the use of additives (Pean et al., 1998; Pean et al., 1999), protein release according to a zero-order profile and without denaturation was scarcely reported (Kim et al., 2006; Park et al., 2006; Lee et al., 2007).

The release of small hydrophobic molecules from PLGA microspheres is governed by drug diffusion through aqueous pores in the initial phase and by polymer degradation at later stages. For proteins, an initial massive release (burst effect) followed by an incomplete release was frequently observed due to instability problems (Crotts et al., 1998; Aubert-Pouessel et al., 2004). Moisture-induced aggregation and ionic interactions were supposed to occur in the initial phase of the microsphere hydration. Later, during polymer erosion, non-specific protein adsorption onto the degrading surface area and covalent/noncovalent aggregation due to the formation of acidic PLGA degradation products were reported as factors responsible for this incomplete release (Park et al., 1998)

The use of stabilizing additives was the most widely employed strategy to minimize protein degradation associated with the direct environment of degrading PLGA (Morlock et al., 1997). However, stabilizers only influenced the first day release because of their rapid diffusion from the microparticles (Sanchez et al., 1999). Alternatively, complex methods were engineered to allow the complete and sustained release of proteins, i.e. protein chemical modification (Castellanos et al., 2005), preparation of heterogeneously structured microspheres (Jiang et al., 2003) and formation of porous microspheres (Kim et al., 2006).

It has now been developed a new method for preparing microencapsulated protein, which allows to obtain a complete and continuous release of the protein in a biologically active form. Advantageously, this method can be easily applied to a wide range of proteins.

More specifically, it has been discovered that when the protein was precipitated in the presence of a poloxamer, particles of protein/poloxamer were formed. Now, these poloxamer-protein particles are particularly advantageous for preparing microspheres loaded with protein, notably by the s/o/w method or by prilling. It has indeed been observed that the solid state protein allows to stabilize the protein during the release step so that the use of stabilizing agents such as albumin or trehalose is not required. Further, precipitation of the protein with poloxamer allows to improve the release profile of the protein from microspheres, notably to obtain a continuous and sustained release of the protein in a biologically active form, notably for at least 20 days. Thus, advantageously, the presence of poloxamer does not induce a burst effect. As poloxamer is a surfactant, it is assumed that its presence limits the interactions between the protein and the polymer which encapsulates the protein, thus enabling to improve the release of the protein.

Poloxamer-protein Particles

Thus, in one aspect, the invention is directed to a method for preparing a dispersion of poloxamer-protein particles, said method comprising the steps of:

i) preparing an aqueous solution comprising a protein and a poloxamer;

ii) contacting the obtained solution with a water-miscible protein non solvent in a sufficient amount to form a dispersion of poloxamer-protein particles;

and optionally iii) recovering the obtained poloxamer-protein particles.

This method is particularly advantageous for preparing non denaturated solid state protein as small poloxamer-protein particles which are particularly useful for subsequent encapsulation. Advantageously, this method can be applied to a wide range of protein with high yields.

As used herein, the term "particles" refers to an aggregated physical unit of solid material.

As used herein, the expression "poloxamer-protein particle" refers to a particle comprising a precipitated protein in combination with a poloxamer, notably one or more molecules of precipitated proteins combined with one or more molecules of poloxamer.

The particles according to the invention are preferably nanoparticles.

Nanoparticles are understood as particles having a median diameter $d_{50}$ inferior to 1 μm.

Preferably, the median diameter of the poloxamer-protein particles of the invention ranges from 50 to 200 nm and is notably of about 150 nm.

As used herein, the terms "median diameter $d_{50}$" refers to the particle diameter so that 50% of the volume of the particles population have a smaller diameter.

The median diameter $d_{50}$ according to the invention is determined by virtue of a particle size measurement performed on the suspensions according to the method based on light diffraction.

As used herein, the term "poloxamer" refers to a nonionic block copolymer comprising a hydrophobic chain of polyoxypropylene and a hydrophilic chain of polyoxyethylene. Such poloxamers may be linear or branched, and include notably tri-blocks or tetra-blocks copolymers. They notably include poloxamines such as Tetronic® 1107 (BASF). Especially preferred poloxamers are those having a hydrophile-lipophile balance (HLB) not less than 10, preferably not less than 18, and most preferably not less than 24. Most preferred poloxamers are ones that are pharmaceutically acceptable for the intended route of administration of the protein particles.

Preferred poloxamers are composed of a central hydrophobic chain of polyoxypropylene flanked by two hydrophilic chains of polyoxyethylene.

Preferably, the poloxamer is selected from the group consisting of poloxamer 188, 407, 338 and 237.

The molar ratio (mol/mol) of poloxamer/protein is not critical for the precipitation of protein and may vary in a wide range.

Preferably, the protein is a therapeutic protein. Examples of suitable proteins include notably enzymes, growth factors, cytokines, hormones, antibodies, fragments of antibodies or coagulation factors. As growth factors, mention may be made of Nerve Growth Factor, Brain Derived Neurotrophic Factor, Neurotrophin 3, the Transforming Growth Factor beta family, the Glial Cell Line-Derived Neurotrophic Factor family, the Fibroblast Growth Factors, Endothelium Growth Factor, Platelet-Derived Growth Factor. Cytokines such as interferon $\alpha$, $\beta$, $\gamma$, hormones such as Human Growth Hormone, Erythropoïetine, interleukins such as IL-1, IL-2, chemokines, antigens and mixture thereof are other examples. The protein could also be a diagnostic agent, a cosmetic or a nutritional supplement.

It has been observed that the precipitation yield of protein according to the invention generally increases with the molecular weight of protein. Thus, the method according to the invention may be applied to a wide range of protein molecular weights.

Preferably, the molecular weight of protein is not less than 8 KDa, more preferably not less than 10 KDa.

As an example, the protein molecular weight may range from 10 to 950 KDa, and notably from 10 to 200 KDa.

The water-miscible protein non solvent is used in a sufficient amount to precipitate the protein as small particles.

A volume ratio of water miscible solvent/aqueous solution ranging from 5 to 100 is generally sufficient to induce the precipitation of the protein in the presence of poloxamer.

The formation of protein-poloxamer particles may occur in a wide range of temperature. Thus, preferably, the water-miscible protein non solvent is contacted with said solution comprising the protein and the poloxamer at a temperature ranging from 1 to 25° C. More preferably, it is contacted at a temperature ranging from 2 to 10° C. and most preferably of about 4° C. Indeed, it has been observed that the formation of protein-poloxamer particles is more reproducible at low temperatures. This may be particularly advantageous when such poloxamer-protein particles are intended to be encapsulated, insofar as poloxamer-protein particles allow to improve the release profile of protein from microspheres or microparticles.

Preferably, the water-miscible protein non solvent is also a non-solvent of the poloxamer.

As used herein, "protein non solvent" or "poloxamer non solvent" means a solvent wherein the protein, the poloxamer respectively precipitates.

The water-miscible protein non solvent is preferably biocompatible.

As used herein, "biocompatible" refers to those solvents which are, within the scope of sound medical judgment, suitable for contact with the tissues of human beings and animals without excessive toxicity, irritation, allergic response, or other problem complications commensurate with a reasonable benefit/risk ratio.

Preferably, the water-miscible non solvent is glycofurol also called tetraglycol or tetrahydrofurfurylpolyethyleneglycol or tetrahydrofurfuryl alcohol, or also polyethyleneglycol ether (CAS: 9004-76-6).

The volume of glycofurol may represent 80% to 99% of the volume of the aqueous solution.

Preferably, the aqueous solution further contains a salt.

Advantageously, the use of a salt in combination with a water-miscible non solvent of the protein promotes and/or enhances the precipitation of the protein. It notably allows to reach better yields of precipitation. Further, protein activity is preserved after precipitation and redissolution which is scarcely observed with salt-induced precipitation.

The salt concentration of the aqueous solution may vary in a wide range. It is generally predetermined according to the nature of the protein.

For a given amount of one protein, at a fixed solution pH, a fixed temperature and a fixed volume ratio of water/water-miscible non solvent, the person ordinary skilled in the art may determine a minimal suitable salt concentration by routine work, typically by adding increasing amounts of salt up to observing the precipitation of the protein. In this respect, it can be noted that the presence of poloxamer does not affect the formation of protein precipitates.

Preferably, the concentration of salt ranges from 0.01M to 3M.

Preferably, the salt is a water soluble electrolyte. Tris [hydroxymethyl]-aminomethane, NaCl, KCl, $(NH_4)_2SO_4$ or a mixture thereof may be used. Among these, NaCl is particularly preferred.

The precipitation yield of the protein may be further optimized by adjusting three parameters: the ratio between the volumes of the aqueous phase and of the water-miscible protein non solvent, the ionic strength and the mass of protein.

As an example, by using optimized conditions, a precipitation yield superior to 95% may be obtained for lysozyme.

The particles may be recovered by using any conventional methods, notably centrifugation.

In a particular aspect of the invention, the water-miscible protein non solvent further contains a dissolved wall-forming polymer. In this respect, the water-miscible protein non solvent is preferably glycofurol.

As used herein, the wording "wall-forming polymer" refers to polymers capable of forming the structural entity of a matrix individually or in combination. Biodegradable and biocompatible wall-forming polymers are preferred, especially for injectable applications. Examples of such polymers include notably poly($\alpha$-hydroxyacides) such as polylactides (PLA), poly(lactide-co-glycolide) copolymers (PLGA's), polyethylene glycol conjugated with a copolymer of lactic acid and glycocolic acid (PLGA'-PEG's) or with a polymer of lactic acid, polyesters such as poly-$\epsilon$-caprolactones, poly(orthoesters) and triglycerides and mixtures thereof.

Preferably, the molar ratio (mol/mol) of poloxamer/polymer ranges from 1 to 30, more preferably from 2 to 10 and is most preferably of about 5.

This embodiment is particularly advantageous as the obtained dispersion may be directly implemented in an encapsulation method such as prilling, without need of recovering the formed poloxamer-protein particles.

In view of encapsulating poloxamer-protein particles and notably of improving the release profile of protein from microspheres or microcapsules, it is particularly preferred to use a molar ratio (mol/mol) of poloxamer/protein in the range of 1 to 30, more preferably of 2 to 20, and most preferably of about 17.

In a further aspect, the invention is directed to a dispersion of poloxamer-protein particles obtainable by the method of the invention.

In a still further aspect, the invention is directed to poloxamer-protein particles obtainable by the method of the invention.

Encapsulated Poloxamer-protein Particles

The poloxamer-protein particles of the present invention can further be encapsulated within matrices of wall-forming polymers to form encapsulated particles. The encapsulation may be accomplished by any process known in the art such as the emulsification/solvent extraction process or the prilling method. In respect of the emulsification/solvent extraction process, reference could be made notably to Pean et al., 1998.

In a preferred aspect, (micro)encapsulation of the particles according to the invention is accomplished by an emulsification/solvent extraction process.

Thus, the invention is directed to a method for encapsulating poloxamer-protein particles comprising:
i) preparing a s/o/w emulsion containing:
as a continuous phase, an aqueous phase, and
as a discontinuous phase, an organic solvent containing dispersed poloxamer-protein particles as defined above and a wall-forming polymer, said wall-forming polymer being soluble in said organic solvent, and insoluble in said continuous phase,
ii) solidifying said discontinuous phase, thereby forming encapsulated poloxamer-protein particles; and optionally
iii) recovering the obtained encapsulated poloxamer-protein particles.

As used herein, the term "emulsion" refers to a heterogenous system of one immiscible liquid (discontinuous phase) dispersed in another liquid (continuous phase) in the form of droplets. The size of the droplets of the emulsion may range from 1 μm to several hundred μm, for example to 100 μm.

As used herein, "s/o/w emulsion" means a solid-in-oil-in-water emulsion and refers to an emulsion wherein poloxamer-protein particles are dispersed in the organic solvent forming the discontinuous phase.

The emulsion may be prepared by any conventional methods which may include notably shearing, high pressure homogenization, static mixing, sonication, phase inversion induced by temperature or/and pressure.

Preferably, the s/o/w emulsion is formed by pouring the discontinous phase in the continuous phase under stirring.

As an example, the organic solvent forming the discontinuous phase may be selected from the group consisting of dichloromethane, acetone, ethyl acetate and chloroform or a mixture thereof.

Preferably, the wall-forming polymer is a polymer of lactic acid, a copolymer of lactic acid and glycolic acid, in particular poly(D,L-lactide-co-glycolide) (PLGA) or polyethylene glycol conjugated PLGA's (PLGA'-PEG's) such as the triblock copolymer PLGA-PEG-PLGA.

Preferably, the continuous phase further comprises a surfactant such as poly(vinyl alcohol).

In a preferred aspect, the solidification of the discontinuous phase is performed by extracting the organic solvent from the discontinuous phase, thus desolvating the wall-forming polymer and solidifying the discontinuous phase.

Preferably, the solvent is extracted by adding a second solvent, said second solvent being miscible with the solvent of the discontinuous phase and not a solvent of the wall-forming polymer contained in the discontinuous phase, thereby forming a mixture of solvents which is miscible in the continuous phase.

As an example, the second solvent may be water, ethanol, propylene glycol or polyethylene glycols.

The obtained encapsulated particles may be recovered by using any conventional methods such as filtration or centrifugation and can be lyophilized after their washing.

In a further preferred aspect, (micro)encapsulation of the particles according to the invention is accomplished by the technique known as laminar jet break-up or "prilling" which is particularly advantageous because it is industrially feasible and induces the formation of monodispersed microparticles (Serp et al., 2000).

Thus, the invention is directed to a method for encapsulating poloxamer-protein particles comprising:
i) providing a dispersion of poloxamer-protein particles containing a wall-forming polymer as defined above or dispersing poloxamer-protein particles as defined above in a solution of a wall-forming polymer dissolved in a solvent;
ii) forming droplets of the dispersion of step i);
iii) solidifying said droplets;
and optionally
iv) recovering the obtained encapsulated poloxamer-protein particles.

Preferably, the droplets are solidified by extracting the solvent of the dispersion.

The solvent of the dispersion may notably be extracted with a second solvent, said second solvent being miscible with the solvent of the dispersion and being a non-solvent of said wall-forming polymer, thereby forming encapsulated poloxamer-protein particles.

Encapsulated poloxamer-protein particles may notably be prepared according to this method, by breaking apart a laminar jet of a dispersion as defined in step i), into monosized droplets by means of a vibrating nozzle device. The obtained droplets may then be solidified by falling into a solidification bath, notably a bath of a second solvent which is a non solvent of the wall-forming polymer and which is miscible with the solvent of the dispersion.

Preferably, the solvent of the dispersion is glycofurol and the wall-forming polymer is PLGA. In this context, the droplets of the dispersion may be solidified notably into a PGLA non-solvent bath of water, ethanol, glycerol, polyethylene glycol, propan-2-ol, propylene glycol or a mixture thereof. This embodiment is particularly advantageous as no toxic solvent is used.

In a still further aspect, the invention is also directed to the encapsulated poloxamer-protein particles obtainable according to the invention.

Encapsulated particles are notably microencapsulated particles, and may be microcapsules or microspheres. As used herein, "microspheres" are matrix systems in which the poloxamer-protein combination is dispersed. "Microcapsules" are composed of a nucleus of poloxamer-protein combination coated with a layer of polymer.

Microcapsules may be obtained with the prilling method, while microspheres may be obtained with the s/o/w emulsification solvent extraction process or by prilling.

Advantageously, the poloxamer-protein combination allows to obtain microspheres in which the protein is homogeneously dispersed in the matrix of wall-forming polymer and thus to improve the release profile of the encapsulated protein.

Preferably, the encapsulated poloxamer-protein particles have a median diameter ranging from 1 to 1000 μm.

Advantageously, the encapsulated poloxamer-protein particles display an improved release profile of the protein as compared to encapsulated protein particles wherein the protein has not been precipitated with a poloxamer. More specifically, it has been observed that encapsulated poloxamer-protein particles according to the invention allow a continuous release of the protein without any burst effect over 20 days.

The invention is also directed to a pharmaceutical composition comprising encapsulated poloxamer-protein particles according to the invention.

FIGURES

FIG. 1: Optimization of the lysozyme precipitation: experimental design. The table represents the values of each factor ($U_1$, $U_2$, $U_3$) for the fifteen experiments.

FIG. 2: Optimization of the lysozyme precipitation: spatial representation of the experimental design results.

Numbers in the circles refer to the percentage of lysozyme recovered under a biologically active form, after precipitation and dissolution, for each experiment.

Figure 3:
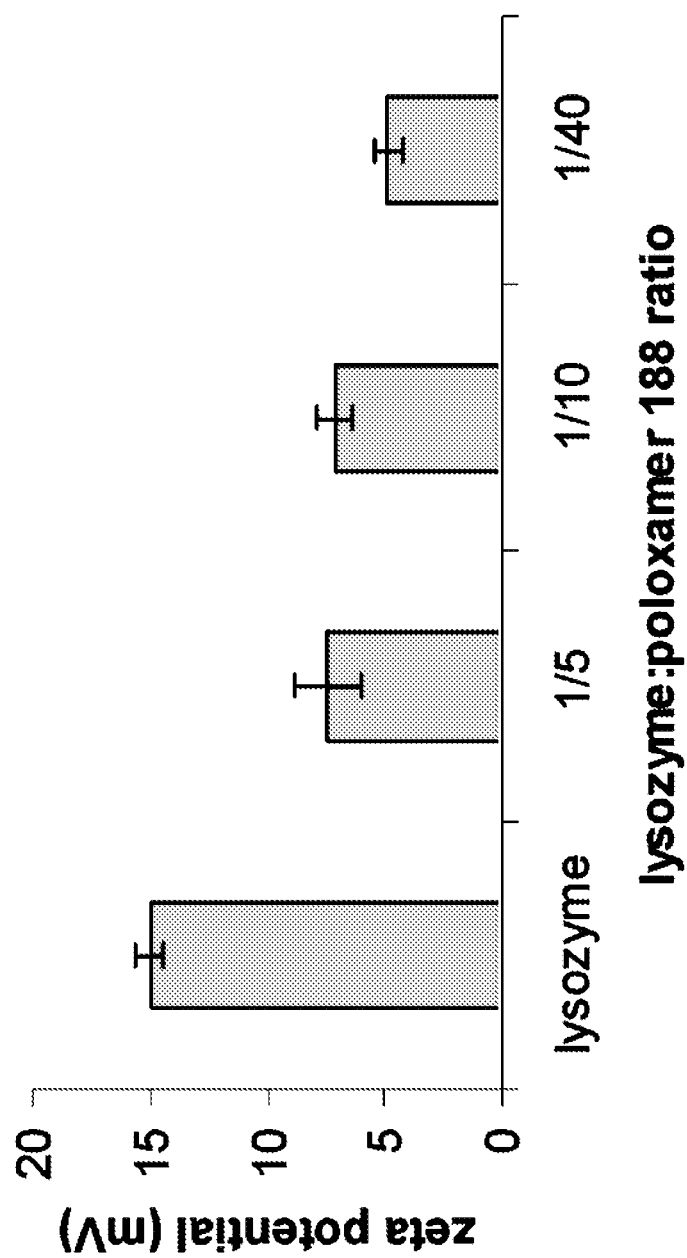

FIG. 3: Evolution of lysozyme zeta potential when adding poloxamer 188 in solution.

Figure 4:
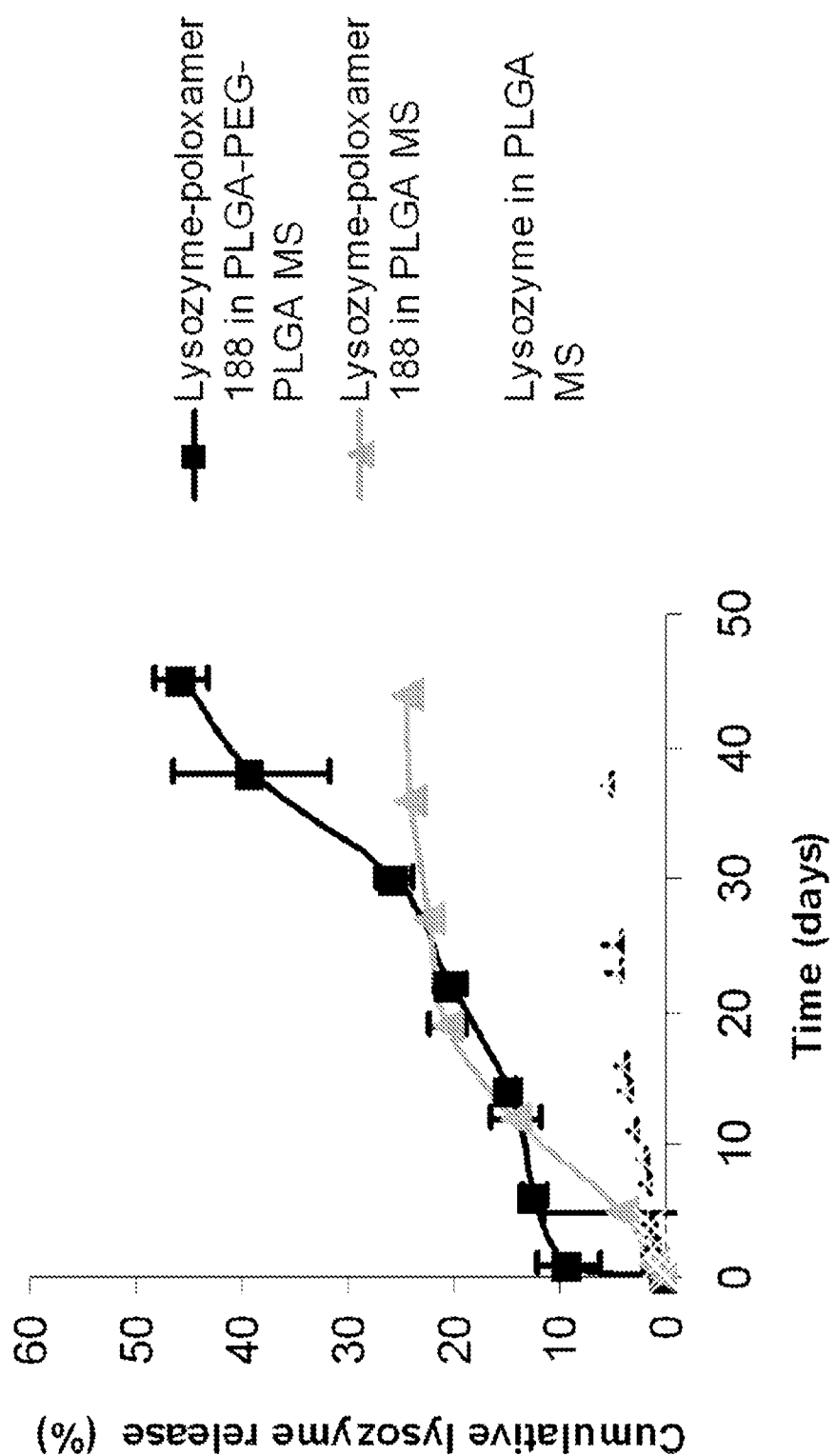

FIG. 4: In vitro release profile of lysozyme (mean±SD) from PLGA microspheres (MS) without poloxamer 188 (2 batches twice) and with poloxamer 188 (example 7) (3 batches) and from PLGA-PEG-PLGA microspheres containing poloxamer 188 (example 9) (7 batches).

Figure 5:
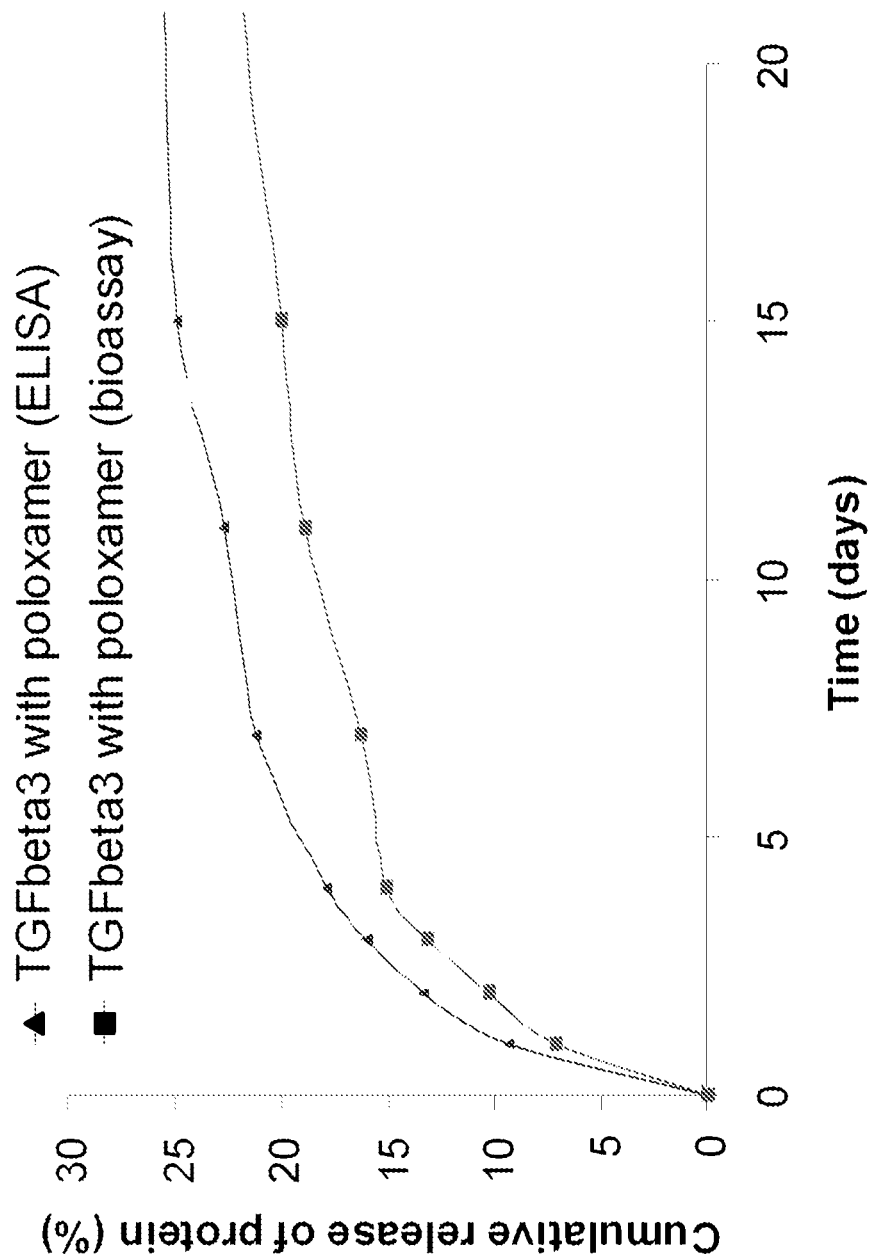

FIG. 5: In vitro release profile of TGF beta 3 with poloxamer 188 from PLGA microspheres assessed by ELISA and biological activity of released TGF beta 3 assessed by a bioassay.

EXAMPLES

Materials

Lysozyme (chicken egg white) and its substrate: *Micrococcus lysodeikticus*, glycofurol (tetraglycol or α-[(tetrahydro-2-furanyl)methyl]-ω-hydroxy-poly(oxy-1,2-ethanediyl) and buffer compounds were obtained from Sigma-Aldrich (Saint Quentin Fallavier, France). TGF beta 3 was purchased from Abcys (Paris, France). TGF beta 3 ELISA kit was from R&D systems (Lille, France). Poloxamer was kindly supplied by BASF (Levallois-Perret, France). Capped 75/25 PLGA, provided by Phusis (Saint-Ismier, France), had a mean molecular weight of 27,000 Da (Polydispersity index, I=1.9) as determined by size exclusion chromatography (standard: polystyrene). PLGA50:50-PEG-PLGA50:50 (RGP t 50106, 10% PEG with 6,000 Da, i.v. 0.75) was purchased from Boehringer-Ingelheim (Ingelheim, Germany). Polyvinyl alcohol (Mowiol® 4-88) was from Kuraray Specialities Europe (Frankfurt, Germany).

Method for Preparing Protein Particles

Firstly, the protein was dissolved in a non-buffered saline solution and then mixed with glycofurol at room temperature. 30 minutes later, the protein particles were recovered by centrifugation (10,000 g, 30 min, 4° C.). Mixing and centrifugation times of 30 min were selected in order to optimize the precipitation yield.

Method for Preparing Protein-poloxamer Particles

Firstly, protein and poloxamer 188 were codissolved in a saline solution. This protein-poloxamer solution was then mixed with glycofurol to prepare a protein-poloxamer dispersion. 30 minutes later, the protein-poloxamer particles were recovered by centrifugation (10,000 g, 30 min, 4° C.). Mixing and centrifugation times of 30 min were selected in order to optimize the precipitation yield.

Optimization of the Precipitation Yield of a Protein Widely Available Such as Lysozyme To define the optimum conditions of precipitation of lysozyme, an experimental design was used. Preliminary studies (not shown) using the technique described revealed that three parameters influence protein precipitation yield: the ratio between the volumes of aqueous phase and of glycofurol, the ionic strength and the mass of protein. The presence of poloxamer does not affect the protein precipitation.

To study these three variables, a Doehlert matrix was chosen. Fifteen experiments were carried out. Each experiment was repeated three times. The experimental domain for each factor is described as follows:

ionic strength of the aqueous phase ($U_1$): 0.01 to 0.59 M (5 levels), volume of the aqueous phase ($U_2$): 25 to 155 µl (7 levels)

protein quantity ($U_3$): 0.1 to 0.9 mg (3 levels).

The volume of glycofurol was the complement for 1 ml of suspension.

Experimental design is reported in FIG. 1.

The measured response was the percentage of reversible lysozyme particles collected (precipitation yield) (FIG. 2). For its determination, the dispersion of protein particles in glycofurol was centrifuged, the supernatant eliminated and the pellet of protein particles dissolved in TRIS-HCl 0.01M buffer, pH 7.4 in order to determine its active mass. Biological activity of lysozyme was determined by measuring the turbidity change in a *Micrococcus lysodeikticus* bacterial cell suspension.

Nemrod® W software (2000, LPRAI, Marseille) was used for generation and exploitation of the statistical experimental design.

Optimization of the Precipitation Yield of a Protein Scarcely Available (TGF-β3)

To define protein behaviour in the presence of salt and glycofurol, a rapid salt screening may be employed. An aqueous protein solution (50 µl) containing the protein quantity wanted to be precipitated (from 20 to 1000 µg) is deposited in the well of a 96-well plate. Then, saline solutions (50 µl) with growing salt concentrations (from 0 to 3M) are added in each well. Finally, glycofurol (300 µl) is adjoined and the absorbance is measured at 350 nm. An increase in the absorbance is related to the formation protein particles. The presence of poloxamer does not affect the formation of protein particles.

Size of the Lysozyme-poloxamer 188 Particles

The size of the lysozyme-poloxamer 188 particles dispersed in glycofurol was determined by light diffraction (Mastersizer® 2000, Malvern Instruments, Worcestershire, UK).

Zeta Potential

To monitor the formation of a combination between lysozyme and poloxamer 188 in solution, lysozyme solution in acetic acid 0.1M containing increasing amount of poloxamer 188 were prepared. The protein concentration was maintained at 10 mg/ml. The corresponding zeta potential was measured as a function of protein to poloxamer ratio, using a Zetasizer Nano-ZS (Malvern Instruments, Worcestershire, UK).

FTIR

The secondary structure of lysozyme with or without poloxamer 188 inside the microspheres was determined by FTIR spectroscopy. Microspheres loaded with 5% w/w of protein (with respect to the amount of PLGA) were studied in order to detect the protein. FTIR studies were conducted with a Bucker IFS 28 equipped with a DTGS detector. 500 scans (4000-400 $cm^{-1}$) at 2 $cm^{-1}$ resolution were averaged to obtain each spectrum. Lyophilized microspheres were measured as KBr pellets (4-5 mg of microspheres per 200 mg of KBr). All spectra were analyzed in the amide I region (1700-1600 $cm^{-1}$) using the program OPUS version 2.0. In all cases, a linear baseline between 2000-1800 $cm^{-1}$ was subtracted. Infrared band position and the number of bands in the amide I region were calculated by Levenberg-Marquardt algorithm using the program OPUS. The secondary structure contents were calculated from the area of the individual assigned bands and their fraction of the total area in the amide I region.

BSA-FITC Distribution in Microsphere

Microspheres were loaded with BSA-FITC or with BSA-FITC/poloxamer 188 as described above. A laser scanning confocal imaging system (Olympus light microscope Fluoview FU300, Paris, France) was employed to observe BSA-FITC distribution in microspheres. Dry microspheres were dispersed on a glass slide; fluorescence images of cross-sections were taken by an optical sectioning. All the images were obtained using a single resolution.

Preparation of the Microencapsuled Lysozyme-poloxamer 188 Particles

PLGA microspheres loaded with lysozyme-poloxamer 188 particles were prepared using a s/o/w emulsion solvent extraction-evaporation process adapted from Pean et al. (Pean et al., 1998). Briefly, 0.9 mg of protein-poloxamer 188 particles (0.6% w/w with respect to the amount of PLGA) were prepared in the optimum conditions of precipitation and collected as described above. Then, they were carefully dispersed in an organic solution (2 ml; 3:1 methylene chloride:acetone) containing 150 mg of PLGA. The resulting organic suspension was then emulsified in a poly(vinyl alcohol) aqueous solution (90 ml, 4% w/v) maintained at 1° C. and mechanically stirred at 550 rpm for 1 min (heidolph RZR 2041, Merck Eurolab, Paris, France). After addition of 100 ml of deionized water and stirring for 10 min, the resulting s/o/w emulsion was added to deionized water (500 ml) and stirred further for 20 min to extract the organic solvent. Finally, the formed microparticles were filtered on a 5 µm filter (HVLP type, Millipore S A, Guyancourt, France), washed five times with 100 ml of deionized water and freeze-dried. The average volume diameter and the size distribution of the resulting microspheres were evaluated using a Multisizer™ 3 Coulter Counter® (Beckman Coulter, Roissy C D G, France).

Lysozyme Encapsulation Efficiency

Protein encapsulation yield was determined considering the biologically-active entrapped protein. Lysozyme PLGA microspheres (10 mg, 3 batches) were dissolved in 0.9 ml DMSO in silanized glass tube. After 1 hour, 3 ml of 0.01M HCl was added. The solution was left to stand for one more hour, and then incubated with *Micrococcus lysodeikticus* suspension for lysozyme activity determination.

In Vitro Release Profile of Lysozyme from Microspheres

The in vitro release profile of lysozyme from PLGA microspheres was determined by adding 500 µL of TRIS-HCl 0.01M buffer, pH 7.4, containing 0.1% w/v BSA and 0.09% w/v NaCl to 10 mg of microspheres into centrifugation tubes. The tubes were closed, incubated in a water bath at 37° C. and agitated at 125 rpm. At determined time intervals, the tubes were centrifuged for 5 min at 3000 rpm. The 500 µl of the supernatant were collected for analysis and replaced by fresh buffer. The percentage of biologically-active released lysozyme was measured by enzymatic assay.

Results

EXAMPLE 1

Preparation of 900 µg of Lysozyme Particles Coupled with Poloxamer 188

45 µl of a solution containing 900 µg of lysozyme and 9 mg of poloxamer 188 in NaCl 0.3 M are added to glycofurol to form a 1 ml suspension at room temperature. The complex particles are recovered by centrifugation (10,000 g, 30 min, 4° C.) and elimination of the supernatant.

EXAMPLE 2

Preparation of 300 µg of Lysozyme Particles Coupled with Poloxamer 188

10 µl of a solution containing 300 µg of lysozyme and 3 mg of poloxamer 188 in NaCl 0.3 M are added to glycofurol to form a 1 ml suspension. The poloxamer-protein particles are recovered by centrifugation (10,000 g, 30 min, 4° C.) and elimination of the supernatant.

EXAMPLE 3

Preparation of 9 mg of Lysozyme Particles Coupled with Poloxamer 188

450 µl of a solution containing 9 mg of lysozyme and 90 mg of poloxamer 188 in NaCl 0.3 M are added to glycofurol to form a 10 ml suspension. The complex particles are recovered by centrifugation (10,000 g, 30 min, 4° C.) and elimination of the supernatant.

EXAMPLE 4

Activity of Lysozyme Particles Coupled with Poloxamer 188 after Dissolution

The pellet of poloxamer-protein particles described in Example 1 and 2 is dissolved in an appropriate solvent in order to determine its active mass (TRIS-HCl 0.01M buffer, pH 7.4). Biological activity of lysozyme is determined by measuring the turbidity change in a *Micrococcus lysodeikticus* bacterial cell suspension. More than 80% of the protein is recovered in an active form.

EXAMPLE 5

Size of the Lysozyme/Poloxamer 188 Particles

The size of the poloxamer-protein particles suspended in glycofurol (described in example 1) was determined by light diffraction. The average particle size is about 100 nm with a narrow distribution.

EXAMPLE 6

Evolution of Lysozyme Zeta Potential in Presence of Poloxamer 188

The interaction of lysozyme with increasing amount of poloxamer 188 in aqueous solution was controlled by zeta potential measurements. When poloxamer 188 was added, lysozyme zeta potential shifts from 15 to 5 mV (FIG. 3). This decrease of the net surface charge on lysozyme may be considered as the result of molecular combination of lysozyme with poloxamer 188.

EXAMPLE 7

Microencapsulation of the Lysozyme/Poloxamer 188 Particles in PLGA Microspheres

Preparation of the PLGA Microspheres Loaded with Lysozyme/Poloxamer 188 Particles Lysozyme-loaded PLGA microspheres were prepared using a solid-in-oil-in-water (s/o/w) emulsion solvent extraction-evaporation process. Briefly, 900 μg of protein particles coupled with poloxamer 188 (0.6% protein w/w with respect to the amount of PLGA) were prepared as described in example 1 and collected as described above. Then, they were carefully dispersed in an organic solution (2 ml; 3:1 methylene chloride:acetone) containing 150 mg of uncapped 75/25 PLGA (mean molecular weight of 27,000 Da, polydispersity index of 1.9). The resulting organic suspension was then emulsified in a poly(vinyl alcohol) aqueous solution (90 ml, 4% w/v) maintained at 1° C. and mechanically stirred at 550 rpm for 1 min. After addition of 100 ml of deionized water and stirring for 10 min, the resulting s/o/w emulsion was added to deionized water (500 ml) and stirred further for 20 min to extract the organic solvent. Finally, the formed microparticles were filtered on a 5 μm filter washed with 500 ml of deionized water and freeze-dried. The resulting microspheres had an average volume diameter of about 60 μm.

In Vitro Release Study

The in vitro release profile of lysozyme from PLGA microspheres was determined by adding 500 μL of TRIS-HCl 0.01M buffer, pH 7.4, containing 0.1% w/v BSA and 0.09% w/v NaCl to 10 mg of microspheres into eppendorf tubes, incubated in a water bath at 37° C., agitated at 125 rpm. At determined time intervals, the tubes were centrifuged for 5 min at 3000 rpm. The 500 μl of the supernatant were collected for analysis and replaced by fresh buffer. The percentage of released biologically-active lysozyme was measured by enzymatic assay. The effect of poloxamer 188 on the in vitro release profile is shown in FIG. 4.

EXAMPLE 8

To characterize the encapsulated protein-poloxamer particles of example 7, the secondary structure of encapsulated lysozyme was characterized by Fourier transform infrared (FTIR) spectroscopy (Table 1). The protein amide I IR infrared spectra were analyzed for the secondary structure composition and the secondary structure was quantified. Firstly, FTIR spectroscopy demonstrated that few protein structural perturbations were induced by the encapsulation and by the presence of poloxamer. Only minor spectral changes occurred in the amide I band (1700-1600 cm$^{-1}$), which is sensitive to protein structure. Analysis of the spectra by Gaussian curve-fitting revealed few change in the α-helical and in β-sheet content; the secondary structure was within the error the same as for the powder prior to encapsulation.

TABLE 1

Secondary structure of lysozyme under various conditions (as determined by FTIR spectroscopy)

| Conditions | α-helix | β-sheet |
|---|---|---|
| Native lysozyme (powder) | 24.5 | 37.9 |
| Lysozyme in PLGA microspheres | 24.9 | 34.9 |
| Lysozyme + poloxamer188 in PLGA microspheres | 23.9 | 20.2 |

EXAMPLE 9

Microencapsulation of the Lysozyme/Poloxamer 188 Particles in PLGA-PEG-PLGA Microspheres (150 mg Microsphere Batch)

PLGA-PEG-PLGA (10% PEG 6 000 Da) was employed. The same procedure as example 7 was followed to prepare the lysozyme-loaded PLGA-PEG-PLGA microspheres except that the mechanically stirring was adjusted to 850 rpm to obtain 60 μm microspheres. The effect of the polymer type on the in vitro release profile is shown in FIG. 4.

EXAMPLE 10

BSA-FITC/Poloxamer 188 Distribution in PLGA-microspheres

Preparation of the BSA-FITC/Poloxamer 188 Particles

45 μl of a solution containing 900 μg of BSA-FITC and 9 mg of poloxamer 188 in NaCl 0.3 M are added to glycofurol to form a 1 ml suspension at room temperature. The complex particles are recovered by centrifugation (10,000 g, 30 min, 4° C.) and elimination of the supernatant.

Preparation of the PLGA Microspheres Loaded with Lysozyme/Poloxamer 188 Particles BSA-FITC loaded PLGA microspheres were prepared according to the procedure described in example 7. Briefly, 900 μg of protein particles coupled with poloxamer 188 (0.6% protein w/w with respect to the amount of PLGA) were carefully dispersed in an organic solution (2 ml; 3:1 methylene chloride:acetone) containing 150 mg of PLGA. The resulting microspheres had an average volume diameter of about 60 μm.

Confocal Analysis

A confocal image system was employed to observe BSA-FITC distribution in microspheres. Dry microspheres were dispersed on a glass slide; fluorescence images of cross-sections were taken by an optical sectioning. The presence of poloxamer revealed a better protein distribution inside the microspheres.

EXAMPLE 11

Preparation of 125 ng of TGF-β3 (Transforming Growth Factor-beta 3) particles coupled with poloxamer 188

100 μl of a solution containing 125 ng of TGF-β3 and 1.25 mg of poloxamer 188 in 10 mM phosphate buffer (pH7, NaCl 2M) were added to 740 mg glycofurol. The complex particles was recovered by centrifugation (10,000 g, 30 min) and elimination of the supernatant. The presence of poloxamer 188 did not affect the precipitation yield as determined by ELISA quantification.

EXAMPLE 12

Preparation of 50 μg of TGF β3 Particles Coupled with Poloxamer 188

1.220 ml of solution containing 50 μg of TGF beta 3 and 3 mg of poloxamer 188 in 10 mM phosphate buffer (pH 7.4, NaCl 2M) are added to 8.68 g of glycofurol; After 30 min, the particles are recovered by centrifugation (10,000 g, 30 min, 4° C.) and elimination of the supernatant.

EXAMPLE 13

Preparation of 50 mg PLGA Microspheres Batch Loaded with Protein/Poloxamer 188 Particles Protein particles coupled with poloxamer 188 were carefully dispersed in an organic solution (670 μl; 3:1 methylene chloride:acetone) containing 50 mg of capped 75/25 PLGA (mean molecular weight of 27,000 Da, polydispersity index of 1.9). The resulting organic suspension was then emulsified in a poly(vinyl alcohol) aqueous solution (30 ml, 4% w/v) maintained at 1° C. and mechanically stirred at 550 rpm for 1 min. After addition of 33 ml of deionized water and stirring for 10 min, the resulting s/o/w emulsion was added to deionized water (167 ml) and stirred further for 20 min to extract the organic solvent. Finally, the formed microparticles were filtered on a 5 μm filter washed with 500 ml of deionized water and freeze-dried. The resulting microspheres had an average volume diameter of about 60 μm.

EXAMPLE 14

Microencapsulation of TGF β3

TGF beta 3 was precipitated as mentioned in example 12.

In parallel, HAS (Human Albumin Serum) particles was prepared: 10 μl of NaCl 0.3 M containing 250 μg HAS are added to 1.077 g of glycofurol. After 30 min, the HAS particles were recovered by centrifugation (10 000 g, 30 min, 4° C.) and elimination of the supernatant.

The HAS particles were dispersed in 3×100 μl polymer organic solution (composition described in example 13), particles of poloxamer-TGF beta 3 were dispersed in the same conditions. Both suspensions were mixed and used to prepare PLGA microspheres as described in example 13.

EXAMPLE 15

TGF-β3 (Transforming Growth Factor-Beta3) Profile Release

TGF beta 3 was encapsulated as mentioned in example 14.

The in vitro release profile of TGF beta 3 from PLGA microspheres was determined by 500 μl of PBS buffer, pH, containing 1% w/v BSA to 10 mg of microspheres into eppendorf tubes, incubated in a bath at 37° C., agitated at 125 rpm. The 500 μl of the supernatant were collected for analysis and replaced by fresh buffer. The percentage of released TGF beta3 was determined by ELISA and the biological activity of released TGF beta 3 was evaluated by a bioassay (FIG. 5).

REFERENCES

Aubert-Pouessel, A. Venier-Julienne, M. C. Clavreul, A. Sergent, M. Jollivet, C. Montero-Menei, C. N. Garcion, E. Bibby, D. C. Menei, P. and Benoit, J. P., 2004. In vitro study of GDNF release from biodegradable PLGA microspheres, J Control Release, 95, 3, 463-75.

Bilati, U. Allemann, E. and Doelker, E., 2005. Strategic approaches for overcoming peptide and protein instability within biodegradable nano- and microparticles, Eur J Pharm Biopharm, 59, 3, 375-88.

Castellanos, I. J. Al-Azzam, W. and Griebenow, K., 2005. Effect of the covalent modification with poly(ethylene glycol) on alpha-chymotrypsin stability upon encapsulation in poly(lactic-co-glycolic) microspheres, J Pharm Sci, 94, 2, 327-40.

Crotts, G. and Park, T. G., 1998. Protein delivery from poly(lactic-co-glycolic acid) biodegradable microspheres: release kinetics and stability issues, J Microencapsul, 15, 6, 699-713.

Jiang, G. Qiu, W. and DeLuca, P. P., 2003. Preparation and in vitro/in vivo evaluation of insulin-loaded poly(acry-loyl-hydroxyethyl starch)-PLGA composite microspheres, Pharm Res, 20, 3, 452-9.

Kim, H. K. Chung, H. J. and Park, T. G., 2006. Biodegradable polymeric microspheres with "open/closed" pores for sustained release of human growth hormone, Journal of Controlled Release, 112, 2, 167-174.

Lee, E. S. Kwon, M. J. Lee, H. and Kim, J. J., 2007. Stabilization of protein encapsulated in poly(lactide-co-glycolide) microspheres by novel viscous S/W/O/W method, Int J Pharm, 331, 1, 27-37.

Morlock, M. Koll, H. Winter, G. and Kissel, T., 1997. Microencapsulation of rh-erythropoietin, using biodegradable poly(D,L-lactide-co-glycolide): protein stability and the effects of stabilizing excepients, Eur J Pharm Bioph, 43, 29-36.

Park, T. G. Yong Lee, H. and Sung Nam, Y., 1998. A new preparation method for protein loaded poly(D,L-lactic-co-glycolic acid) microspheres and protein release mechanism study, J Control Release, 55, 2-3, 181-91.

Park, J. H. Ye, M. Yeo, Y. Lee, W. K. Paul, C. and Park, K., 2006. Reservoir-type microcapsules prepared by the solvent exchange method: effect of formulation parameters on microencapsulation of lysozyme, Mol Pharm, 3, 2, 135-43.

Pean, J. M. Boury, F. Venier-Julienne, M. G. Menei, P. Proust, J. E. and Benoit, J. P., 1999. Why does PEG 400 co-encapsulation improve NGF stability and release from PLGA biodegradable microspheres, Pharm Res, 16, 8, 1294-9.

Pean, J. M. Venier-Julienne, M. G. Boury, F. Menei, P. Denizot, B. and Benoit, J. P., 1998. NGF release from poly(D,L-lactide-co-glycolide) microspheres. Effect of some formulation parameters on encapsulated NGF stability, J Control Release, 56, 1-3, 175-87.

Sanchez, A. Villamayor, B. Guo, Y. McIver, J. and Alonso, M. J., 1999. Formulation strategies for the stabilization of tetanus toxoid in poly(lactide-co-glycolide) microspheres, Int J Pharm, 185, 2, 255-66.

Schwendeman, S. P. Cardamone, M. Klibanov, A. Langer, R. and Brandon, M. R., 1996. Stability of proteins and their delivery from biodegradable polymer microspheres. In: Cohen, S, and Bernstein, H. (Ed.), Microparticulate systems for the delivery of proteins and vaccines, Marcel Dekker, New York, pp. 1-49.

Serp, D. Cantana, E. Heinzen, C. Von Stockar, U. and Marison, I. W., 2000. Characterization of an encapsulation device for the production of monodisperse alginate beads for cell immobilization, Biotechnol Bioeng, 70, 1, 41-53.

Tamber, H. Johansen, P. Merkle, H. P. and Gander, B., 2005. Formulation aspects of biodegradable polymeric microspheres for antigen delivery, Advanced Drug Delivery Reviews, 57, 3 SPEC. ISS., 357-376.

Van de Weert, M. Hennink, W. E. and Jiskoot, W., 2000. Protein instability in poly(lactic-co-glycolic acid) microparticles, Pharm Res, 17, 10, 1159-67.

Wang, W., 2005. Protein aggregation and its inhibition in biopharmaceutics, Int J Pharm, 289, 1-2, 1-30.

The invention claimed is:
1. A method for preparing a dispersion of poloxamer-protein particles, said method comprising the steps of:
    i) preparing an aqueous solution comprising a protein and a poloxamer; and
    ii) contacting the obtained solution with a water-miscible protein non-solvent in a sufficient amount to form a dispersion of poloxamer-protein particles, wherein the water-miscible protein non-solvent is glycofurol and wherein said poloxamer-protein particles are solid.

2. The method of claim 1, wherein the poloxamer is selected from the group consisting of poloxamer 188, 407, 338 and 237.

3. The method of claim 1, wherein the aqueous solution further contains a salt.

4. The method of claim 3, wherein the salt is present in a concentration ranging from 0.01 to 3M.

5. The method of claim 3, wherein the salt is NaCl.

6. The method of claim 1, wherein the protein is a therapeutic protein.

7. The method of claim 6, wherein the protein is an enzyme, a growth factor, a cytokine, a hormone, an antibody, an antibody fragment or a coagulation factor.

8. The method of claim 1, wherein the poloxamer-protein particles are recovered after centrifugation.

9. The method of claim 1, wherein the water-miscible protein non-solvent further contains a dissolved wall-forming polymer.

10. The method of claim 1, further comprising the step of iii) recovering the obtained poloxamer-protein particles.

11. A dispersion of poloxamer-protein particles obtainable according to claim 1.

12. The dispersion according to claim 11, wherein the water-miscible protein non-solvent, further contains a dissolved wall-forming polymer.

13. Poloxamer-protein particles obtainable according to claim 1.

14. The protein particles according to claim 13, of which median diameter ranges from 50 to 200 nm.

15. A method for encapsulating poloxamer-protein particles comprising:
   i) preparing a s/o/w emulsion containing:
      as a continuous phase, an aqueous phase, and
      as a discontinuous phase, an organic solvent containing dispersed poloxamer-protein particles according to claim 13 and a wall-forming polymer, said wall-forming polymer being soluble in said organic solvent, and insoluble in said continuous phase, and
   ii) solidifying said discontinuous phase, thereby forming encapsulated poloxamer-protein particles.

16. The method of claim 15, wherein the wall-forming polymer is a polymer of lactic acid, a copolymer of lactic acid and glycolic acid or a polyethylene glycol conjugated with a copolymer of lactic acid and glycolic acid or with a polymer of lactic acid.

17. The method of claim 16, wherein the wall-forming polymer is poly(D,L-lactide-co-glycolide) (PLGA) or PLGA-PEG-PLGA.

18. The method of claim 15, further comprising the step of iii) recovering the obtained encapsulated poloxamer-protein particles.

19. A method for encapsulating poloxamer-protein particles comprising:
   i) providing a dispersion of poloxamer-protein particles obtainable according to claim 1, wherein the water-miscible protein non-solvent further contains a dissolved wall-forming polymer or dispersing poloxamer-protein particles obtainable according to claim 1 in a solution of a wall-forming polymer dissolved in a solvent;
   ii) forming droplets of the dispersion of step i); and
   iii) solidifying said droplets.

20. The method of claim 19, wherein the droplets are solidified by extracting the solvent of the dispersion.

21. The method of claim 19, further comprising the step of iv) recovering the obtained encapsulated poloxamer-protein particles.

22. Encapsulated poloxamer-protein particles obtainable according to claim 15.

23. A pharmaceutical composition comprising encapsulated poloxamer-protein according to claim 22.

* * * * *